United States Patent [19]

Kira

[11] Patent Number: 5,290,253
[45] Date of Patent: Mar. 1, 1994

[54] CAP FOR MEDICAL TOOL CONNECTION AND MEDICAL TOOL

[75] Inventor: Norisuke Kira, Fujinomiya, Japan

[73] Assignee: Terumo Kabushiki Kaisha, Tokyo, Japan

[21] Appl. No.: 970,987

[22] Filed: Nov. 2, 1992

Related U.S. Application Data

[63] Continuation of Ser. No. 535,723, Jun. 11, 1990, abandoned.

[30] Foreign Application Priority Data

Jun. 9, 1989 [JP] Japan .................. 1-145225

[51] Int. Cl.⁵ .............................................. A61M 5/00
[52] U.S. Cl. ............................................... 604/190
[58] Field of Search ............... 604/256, 283, 285, 126, 604/122, 190, 405, 406, 905, 86; 210/232, 463; 138/41

[56] References Cited

U.S. PATENT DOCUMENTS

| | | | |
|---|---|---|---|
| 1,314,374 | 8/1919 | Stair | 210/463 |
| 2,313,219 | 3/1943 | Bulling | 604/405 X |
| 2,864,366 | 12/1958 | Miskel | 604/190 |
| 3,070,089 | 12/1962 | Dick | 604/190 X |
| 3,157,481 | 11/1964 | Bujan | 604/190 X |
| 3,307,552 | 3/1967 | Strawn | 604/256 |
| 3,938,520 | 2/1976 | Scislowicz et al. | 604/405 |
| 3,957,654 | 5/1976 | Ayres | 210/516 |
| 4,083,707 | 4/1978 | Wiley | 604/190 X |
| 4,227,527 | 10/1980 | DeFrank et al. | 604/208 |
| 4,287,065 | 9/1981 | Raines | 210/445 |
| 4,291,701 | 9/1981 | Bowman | 604/122 X |
| 4,445,896 | 5/1984 | Gianturco | 604/256 |
| 4,485,014 | 11/1984 | Gilroy et al. | 210/433.2 |
| 4,531,937 | 7/1985 | Yates | 604/53 |
| 4,588,402 | 5/1986 | Igari et al. | |
| 4,668,271 | 5/1987 | Goode et al. | |
| 4,820,288 | 4/1989 | Isono et al. | |
| 4,917,671 | 4/1990 | Chang | 604/168 |
| 4,991,629 | 2/1991 | Ernesto et al. | 138/89 |
| 5,045,096 | 9/1991 | Quang et al. | 55/159 |
| 5,139,031 | 8/1992 | Guirguis | 128/771 |

FOREIGN PATENT DOCUMENTS

| | | | |
|---|---|---|---|
| 0111723 | 6/1984 | European Pat. Off. | 604/86 |
| 3515665 | 5/1986 | Fed. Rep. of Germany | 604/283 |

*Primary Examiner*—Jerome L. Kruter
*Attorney, Agent, or Firm*—Frishauf, Holtz, Goodman & Woodward

[57] ABSTRACT

A cap for a connector in a medical tool, which cap comprises a blind cylindrical body provided on the bottom part thereof with means for closing an open end of a connector member to be capped and an air permeable filter member disposed in said closing means, and a medical tool possessing a tube closed at one end thereof and provided at the other end thereof with a connector member and having an open end of said connector member covered with the cap.

17 Claims, 2 Drawing Sheets

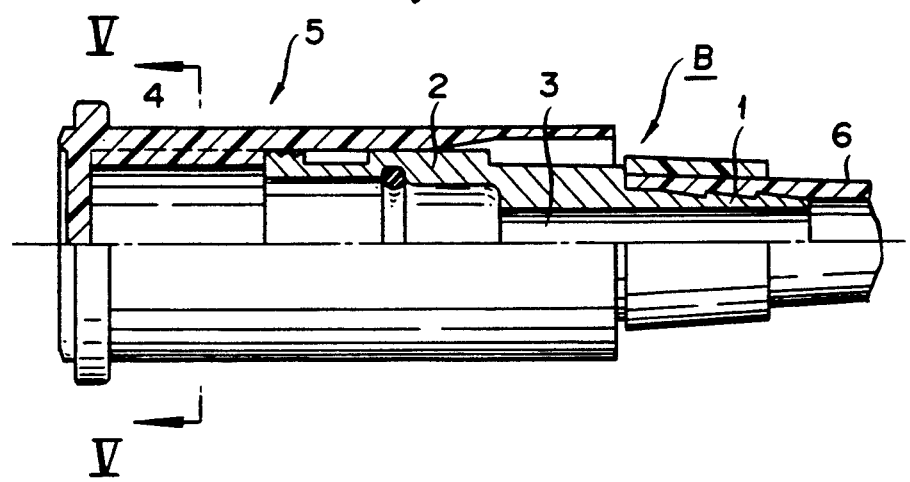
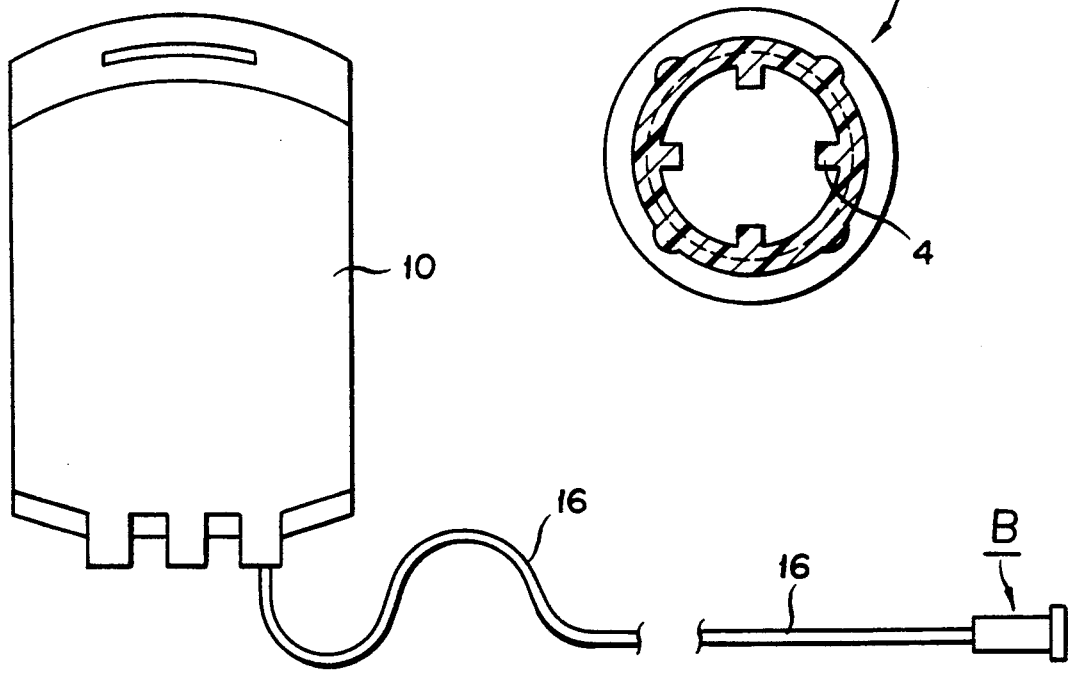

CAP FOR MEDICAL TOOL CONNECTION AND MEDICAL TOOL

This application is a continuation of application Ser. No. 07/535,723, filed Jun. 11, 1990, now abandoned.

BACKGROUND OF THE INVENTION

1. Field of the Invention

This invention relates to a cap for use with a medical tool connector. More particularly, it relates to a cap for use with such a medical tool connector as a connector of the type to be fitted to the leading end of a tube extended as a connector from a dialytic liquid bag which is used as in the method of peritoneal dialysis, for example.

2. Description of the Prior Art

In the mutual connection of tubes or in the connection of a tube to a container or to a catheter involved in preparation for the continuous therapy such as peritoneal dialysis, solution transfusion, or blood transfusion, perfect prevention of the tube interior from ingression of microorganisms poses itself a technical task. Particularly in the peritoneal dialysis, a therapy to be performed at such a site as the abdominal cavity which has absolutely no ability to protect against microorganisms infallible prevention of the ingression of microorganisms through the tube into the abdominal cavity is regarded as an absolute technical task. The latest therapy by peritoneal dialysis is such that the apparatus and tools to be used therefor are not voluminous and the cost incurred thereby is conspicuously small as compared with the dialysis resorting to an artificial kidney. Since the cause for peritoneal coalescence has been substantially elucidated, the peritoneal dialysis can be performed without inducing peritoneal coalescence. Moreover, the therapy itself has been developed to the extent of appreciably lowering the burden exerted on the patient. Further, the method of continuously applicable peritoneal dialysis (CAPD method) which allows the patient to take an uninterrupted treatment while continuing his work has been invented and employed widely for practical use. In these advantageous circumstances, this therapy has been reawakening interest and attracting attention. The reliability of this method of dialysis with respect to the safety of life hinges on the question as to whether or not the ingression of microorganisms such as bacteria and viruses into the tube can be infallibly prevented and, consequently, the complication of peritonitis due to the propagation of such microorganisms within the abdominal cavity can be avoided. It is held at present that protracted performance of this therapy is not completely feasible.

As a typical example, the conventional method of continuously applicable peritoneal dialysis will be described below. By a surgical operation, a catheter is implanted in a patient's abdominal cavity and a connector member is attached to the extracorporeal end of the implanted catheter or the catheter having the connector member is attached in advance thereto is wholly implanted in the patient's abdominal cavity. Then, a connector member attached to the leading end of a tube of a dialytic liquid bag is connected to the connector member of the implanted catheter either directly or through the medium of a tube having connector members attached one each to the opposite ends thereof. The bag is suspended at a prescribed height higher than the abdominal cavity so that the dialytic liquid contained in the bag will flow down into the catheter and induce the dialysis aimed at. In this case, for the purpose of preventing the ingression of microorganisms during the course of the connection of the connector members, the two connector members, for example, are sterilized with flame and connected to each other by shrinkage fit.

The dialytic liquid bag is stowed in a packing container in conjunction with a dialytic liquid discharge tube attached to the bag and provided at the leading end thereof with a connector member and is preserved in a wholly sterilized state. Further, this connector member is designed so as to keep the tube in a thoroughly sterilized state even after the cap is attached thereto and the packing container is opened.

The conventional cap for the connector is made of a heat-resistant corrosionproof metal, as illustrated in FIG. 4 and FIG. 5, in the shape of a blind cylindrical cap 5 provided at one end thereof with a tube insertion terminal part 1 having a substantially equal diameter in the direction of the terminal, at the other end thereof with a female insertion terminal part 2 capable of continuously accommodating therein a male insertion terminal part of another connector member (not shown), and in the interior thereof with a stopper 4 comprising a plurality of ridges 4 formed on the lower inner wall surface so as to be inserted into a female connector member B formed in the shape of a short tube possessing a flow path 3 communicating with the aforementioned other connector member (U.S. Pat. Nos. 4,588,402, 4,668,271, and 4,820,288).

When the dialytic solution bag has the conventional cap of this description fitted around the connector member B at the leading end of the flexible tube 6 of the bag, it is set in place in a packing container (such as, for example, a bag of flexible vinyl chloride resin), sealed hermetically, and subjected to about 30 minutes' steam sterilization in an autoclave at 120° C. In consequence of this sterilization in the autoclave, the interior of the dialytic liquid bag is sterilized by the fact that the steam permeating into the container passes through the flexible tube wall and finds its way into the interior of the tube 6 and the interior of the flow path 3 of the connector member B.

The cap intended to protect the connector member at the leading end of the flexible tube is inherently desired to be capable of substantially completely sealing the connector member so as to keep the interior of the connector member and the interior of the tube in an aspectic state until immediately before use. When the dialytic liquid bag using the cap of this nature is sterilized in the autoclave, the steam entrapped in the hermetically sealed bag is condensed after completion of the sterilization. This condensation of steam has the possibility of crushing or flattening the flexible tube and even inducing the phenomenon of blocking of the flexible tube. When the sterilization is carried out with ethylene oxide gas, it is difficult to sterilize the interior of the flexible tube perfectly because this gas does not have enough ability to permeate into the flexible tube.

The problems mentioned above have been heretofore precluded by providing the cap with ribs or recesses adapted to permit passage of air or forming grooves in the connector member. Logically, these measures may well be regarded as disadvantages from the standpoint of maintenance of the aspectic state mentioned above.

Moreover, since this cap is generally made of such thermoplastic resin as polypropylene and, therefore, is thermally shrunken under the influence of the autoclave sterilization, it must be molded in a slightly larger size enough to make up for this shrinkage. It has occurred at times that the cap will slip off the connector member between the time the cap is attached to the connector member and the time the dialytic liquid bag placed in the autoclave undergoes the sterilization.

An object of this invention, therefore, is to provide a novel cap for the connector used in the medical tool.

Another object of this invention is to provide a cap for the connector in the medical tool, which cap has only a small possibility of slipping off the connector member during the course of sterilization.

SUMMARY OF THE INVENTION

The objects described above are accomplished by a cap for the connector in the medical tool, which cap comprises a blind cylindrical body provided on the bottom thereof with means of closing an open end of a connector member desired to be capped and an air permeable filter member disposed on said closing means.

The present invention also discloses a cap for the connector in the medical tool, wherein the closing means is so constructed as to be projected from the bottom of the cylindrical body toward the open end thereof in the shape of a tube coaxially relative to the cylindrical body and to be inserted into the open end of the connector member. The present invention further discloses a cap for the connector in the medical tool, wherein the filter member is disposed so as to close an open part formed in the bottom part of the tubularly projected part. The present invention further discloses a cap for the connector in the medical tool, wherein the tubularly projected part is formed integrally with the cylindrical body. The present invention further discloses a cap for the connector in the medical tool, wherein the tubularly projected part is made of thermoplastic resin. The present invention further discloses a cap for the connector in the medical tool, wherein the outer leading end part of the tubularly projected part is formed in a converging shape.

The present invention further discloses a medical tool, characterized by the fact that the medical tool is provided with a tube having one end thereof closed and the other end thereof fitted with a connector member and a cap for the connector in the medical tool constructed as described above is fitted around the open end of the connector member. The present invention is directed to a cap for the connector in the medical tool, which cap comprises a blind cylindrical body provided on the bottom part thereof with means of closing an open end of a connector member desired to be capped and a filter member disposed on the closing means. Owing to this construction, even when the medical tool is sterilized with high-pressure steam in an autoclave and the steam entrapped inside the tool is condensed after completion of the sterilization, the medical tool has no possibility of being crushed because air flows into the tube through the filter member. When the medical tool is left standing between the time the packing container is opened prior to the use of the medical tool and the time the cap is removed from the medical tool or when the tube is pressed or bent so as to inhale or exhale air, the possibility of the tube interior being contaminated with microorganisms is nil because the filter member filtrates the air.

When the closing means is constructed so as to be projected from the bottom part of the cylindrical body to the open end thereof in the shape of a tube coaxially relative to the cylindrical body and to be inserted into the open end of the connector member, since the tubularly projected part can be molded in a size suitable for tight fit, it perfectly fits the connector member after the sterilization owing to the shrinkage of the cap. Thus, the present invention has given a solution to the problem that the cap of the conventional construction molded in a slightly large size for insertion around the connector member and allowed to shrink fit it under the thermal influence of sterilization is liable to come off the connector member prior to the sterilization.

BRIEF DESCRIPTION OF THE DRAWINGS

FIG. 4 is a cross section illustrating the state in which the conventional cap is fitted around a connector member, FIG. 5 is a cross section taken through FIG. 4 along the line V—V, and FIG. 6 is a diagram typically illustrating a medical tool possessing a connector around which the cap of the present invention is to be fitted.

EXPLANATION OF THE PREFERRED EMBODIMENT

Figure 1:
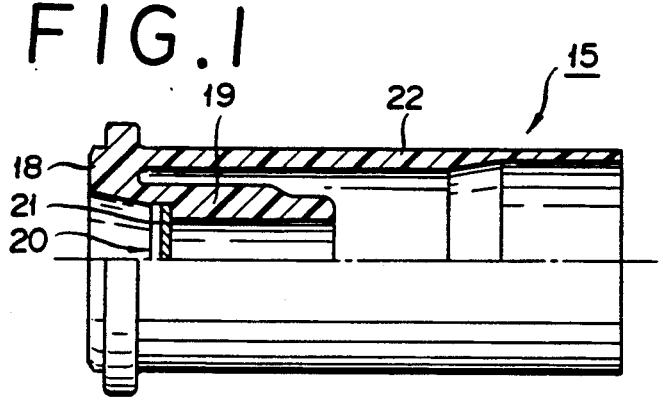
FIG. 1 is a half-sectioned side view of a cap for a connector in a medical tool according with the present invention.
Figure 2:
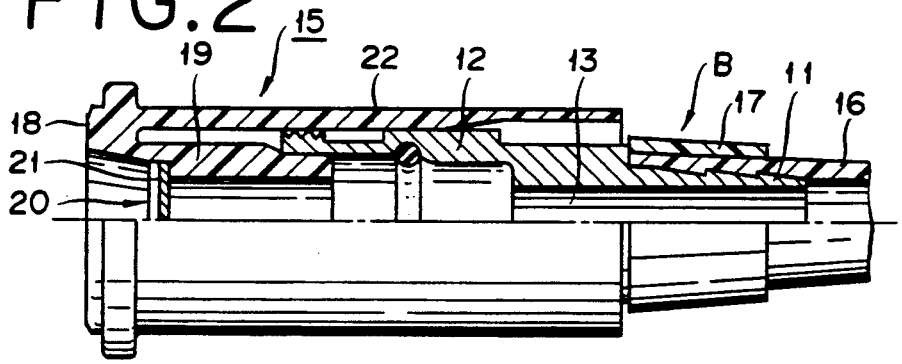
FIG. 2 is a half-sectioned side view of the cap in the state having a connector member inserted therein.

Now, one embodiment of the present invention applied to a connector member at the leading end of a tube communicating with a dialytic solution bag will be described below with reference to the accompanying drawing. A female connector member B is connected through the medium of a tube insertion terminal part 11 as illustrated in FIG. 2 to a dialytic liquid passing tube 16 having one end thereof connected to a dialytic liquid bag 10 as illustrated in FIG. 6, retained in place with an annular retaining member 17, and provided in the interior thereof with a flow path 13. An open end of an inserted part 12 of the female connector member B is closed with closing means which is formed in a cap proper. The closing means, for example, is a tubularly projected part (tubular member) 19 which, as illustrated in FIG. 1 and FIG. 2, is projected from the bottom part of a cylindrical body 15 as a main body of the cap coaxially relative to the cylindrical body 15. An air permeable filter member 21 is attached fast to an open part 20 formed in a bottom part 18 of the tubularly projected part 19.

The connector member B is inserted between an outer barrel 22 of the cylindrical body 15 and the tubularly projected part 19 formed inside the outer barrel 15. An open end of the connector member B is inserted tightly around the tubularly projected part 19. On the other hand, it is inserted rather loosely in the outer barrel 22 in consideration of the shrinkage expected to occur under the thermal influence of sterilization in an autoclave. Since the open end of the connector member B is tightly inserted around the tubularly projected part 19 as described above, the connector part B is preferable to have the outer leading end part thereof formed in a converged shape.

The cap, as a whole, is preferable from the standpoint of airtightness of contact with the connector member B and price to be made of thermoplastic resin such as polypropylene, polyethylene, vinyl chloride resin, or polystyrene, for example. The outer barrel 22 and the tubularly projected part 19 are preferable to be integrally formed. The air permeable filter member 21 is formed of filter paper or nonwoven fabric, for example, and is fastened by adhesion, fusion, or other means to the open part 20 formed in the bottom part.

The dialytic solution bag (not shown) having the connector member B thereof covered with the cap of this invention as illustrated in FIG. 2 is stowed in a packing container (not shown), hermetically sealed therein, and then sterilized in an autoclave at temperature of 120° C., for example, for about 30 minutes. At this time, the steam in the autoclave permeates the wall of the packing container (bag of flexible vinyl chloride resin, for example) and enters the container interior and, at the same time, permeates through the wall of the flexible tube (tube of flexible vinyl chloride resin, for example) and enters the tube interior and also finds its way into the passage of the connector member, to effect sterilization of the entire container. After the autoclave sterilization is completed, the partial pressure of steam inside the tube is greatly lowered because the steam inside the tube is condensed. Since the air inside the packing container passes through the filter member and flows into the tube interior, however, the possibility of the tube being crushed or blocked is perfectly nil.

Figure 3:
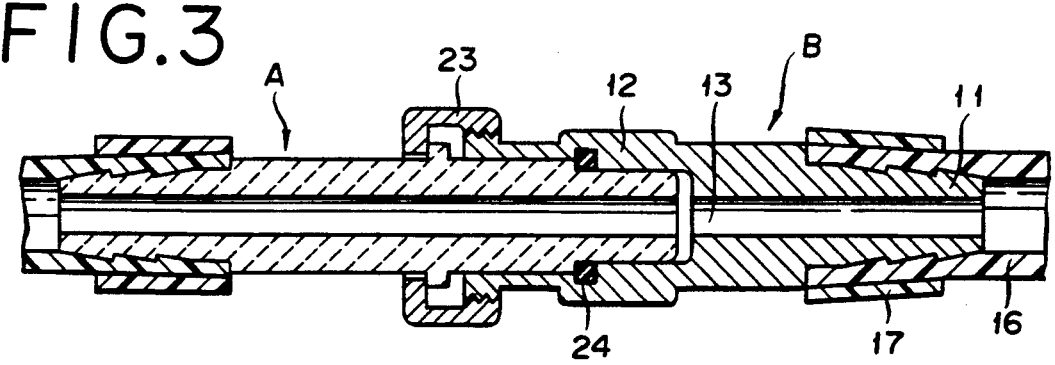
FIG. 3 is a cross section illustrating the state in which two connector members are joined to each other.

The method of continuously applicable peritoneal dialysis (CAPD method) by the use of the dialytic solution bag is effected by opening the packing container, removing the cap, subjecting the connector member A (FIG. 3) connected to the catheter retained inside the peritoneum and the connector member B stripped of the cap to flame sterilization with an alcohol lamp, then inserting an insertion terminal part 25 of a male connector member A into the female connector member B, locking the two connector members with a locking member 23, and sealing the locked joint watertightly with an O-ring 24.

The connector members A and B are both preferable to be made of a heat-resistant corrosionproof material because they are subjected to the flame sterilization prior to use. The materials which fulfil the requirement include metals, ceramics, and heat-resistant resins, for example. Since these connector members are joined by shrink fit of one sort, it is desirable to have one of them made of a metallic material and the other member made of a ceramic material. It is particularly desirable to have the female connector member made of a metallic material and the male connector member made of a ceramic material. The metallic materials which are usable herein include stainless steel, titanium alloy, nickel, nickel alloy, and chromium-plated brass, for example. The ceramic materials which are usable herein include zirconia, silicon nitride, alumina, steatite, forsterite, silicon carbide, and silica, for example.

Example

An open end of a female connector member B made of nickel alloy, attached to the leading end of a tube of flexible vinyl chloride resin of a CAPD grade dialytic solution bag, and fixed in place with an annular retaining member 17 as illustrated in FIG. 1 and FIG. 2 was inserted around a tubularly projected part 19 of a cap provided with closing means projected from the bottom part of a cylindrical body of the cap coaxially relative to the cylindrical body and a filter member 21 disposed in an opening 20 formed in the bottom part. The dialytic liquid bag provided with the connector member B covered with the cap as described above was stowed and hermetically sealed in a bag obtained by superposing two sheets each of a three-layer construction of polypropylene-nylon-polypropylene and fusing the edges of the superposed sheets and subjected to autoclave sterilization at 120° C. for about 30 minutes. In the test runs using the cap of the present invention, absolutely no separation of the cap occurred during the course of autoclave sterilization.

What is claimed is:

1. A cap for a connector in a medical tool to be sterilized in an autoclave, one end of said connector being connected to one end of a tube, and another end of said tube being closed, said cap comprising:
   a connector in a medical tool;
   an outer cylinder;
   an inner cylinder concentrically positioned within said outer cylinder;
   an annular cap portion securing said inner cylinder within said outer cylinder with a predetermined clearance between said inner and outer cylinders, said clearance allowing said outer and inner cylinders to be in tight engagement with an inner peripheral portion of said connector, while also allowing said outer cylinder to be in loose engagement with an outer peripheral portion of said connector, said loose engagement of said outer cylinder with the outer peripheral portion of said connector enabling shrinkage to occur therebetween during an autoclave sterilization; and
   a gas permeable filter member mounted in an open substantially central space of said annular cap portion for closing an end of said concentrically positioned cylinders secured by said annular cap portion, said gas permeable filter member preventing said tube from being deformed due to a condensation of steam remaining in said tube after said autoclave sterilization is completed.

2. A cap as set forth in claim 36, wherein the outer diameter of said inner cylinder is dimensioned such that said inner peripheral portion of said connector tightly engages an outer peripheral portion of said inner cylinder, and the inner diameter of said outer cylinder is dimensioned such that said outer peripheral portion of said connector loosely engages an inner peripheral portion of said outer cylinder.

3. A cap as set forth in claim 1, wherein said outer and inner cylinders and said annular cap portion are integrally formed with each other.

4. A cap as set forth in claim 3, wherein said outer and inner cylinders and said annular cap portion are made of a thermoplastic resin.

5. A cap as set forth in claim 4, wherein said thermoplastic resin is selected from the group consisting of polypropylene, polyethylene, vinyl chloride resin and polystyrene.

6. A cap as set forth in claim 1 wherein said filter member is made of a filter paper.

7. A cap as set forth in claim 1, wherein said filter member is made of a nonwoven fabric.

8. A medical tool device to be sterilized in an autoclave, said medical tool device comprising:
   a tube, one end of which is closed;
   a connector, one end of which is connected to another end of said tube; and
   a cap comprising:

a cylindrical cap body for receiving therein said connector;

engaging means inside said cap body and coupled to said cap body for defining an annular space within said cap body, said engaging means engaging both inner and outer surfaces of a peripheral free end portion of said connector which is inserted into an opening in said cap body and into said annular space; and a gas permeable filter member for closing an open end of said cap body while preventing said tube from being deformed due to a condensation of steam remaining in said tube after a sterilization in an autoclave;

a size of said annular space within said cap body being such that said engaging means is simultaneously:

in tight engagement with said inner surface of said peripheral free end portion of said connector; and in loose engagement with said outer surface of said peripheral free end portion of said connector; and said loose engagement of the engaging means with said outer surface of said peripheral free end portion of said connector enabling shrinkage to occur therebetween during said sterilization in said autoclave.

9. A medical tool device as set forth in claim 8, wherein said engaging means comprises a tubular projecting member inside said cylindrical cap body and being spaced from an inner surface of said cap body, said tubular member having an outer surface which engages said inner surface of said peripheral free end portion of said connector, and said outer surface of said peripheral free end portion of said connector engaging said inner surface of said cap body.

10. A medical tool device as set forth in claim 9, wherein said tubular member and said cap body are integrally formed with each other.

11. A medical tool device as set forth in claim 10, wherein said engaging means comprises a tubular projecting member inside said cylindrical cap body and being spaced from an inner surface of said cap body, said tubular member having an outer surface which engages said inner surface of said peripheral free end portion of said connector, and said outer surface of said peripheral free end portion of said connector engaging said inner surface of said cap body.

12. A medical tool device as set forth in claim 11, wherein said tubular member and said cap body are integrally formed with each other.

13. A medical tool device as set forth in claim 8, wherein said one end of said tube is connected to a bag.

14. A medical tool device as set forth in claim 8, wherein said connector is made of a material selected from the group consisting of a metal, a ceramic and a heat resistant resin.

15. A medical tool as set forth in claim 14, wherein said metal is selected from the group consisting off stainless steel, titanium alloy, nickel, nickel alloy and chromium-plated brass.

16. A medical tool device as set forth in claim 14, wherein said ceramic is selected from the group consisting of zirconia, silicon nitride, alumina, steatite, forsterite, silicon carbide and silica.

17. A medical tool device as set forth in claim 8, wherein said one end of said connector has a tapered end portion that is connectable to said tube.

* * * * *

UNITED STATES PATENT AND TRADEMARK OFFICE
CERTIFICATE OF CORRECTION

PATENT NO. : 5,290,253

DATED : March 1, 1994

INVENTOR(S) : KIRA, Norisuke

It is certified that error appears in the above-identified patent and that said Letters Patent is hereby corrected as shown below:

Title page, Section [56] References Cited;
under "U.S. PATENT DOCUMENTS"

"4,083,707" should be --4,083,706--

Column 8, line 25 (claim 15), "off" should be --of--

Signed and Sealed this

Twenty-third Day of May, 1995

*Attest:*

BRUCE LEHMAN

*Attesting Officer*     *Commissioner of Patents and Trademarks*